United States Patent
Riondel et al.

(10) Patent No.: US 6,469,204 B2
(45) Date of Patent: Oct. 22, 2002

(54) ACRYLATES COMPRISING SEVERAL QUATERNARY AMINO GROUPS IN THE ALCOHOL PART, THEIR PROCESS OF MANUFACTURE AND THE (CO) POLYMERS OBTAINED FROM THESE MONOMERS

(75) Inventors: Alain Riondel, Forbach; Vladimir Chaplinski, Saint Avold, both of (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/984,628

(22) Filed: Oct. 30, 2001

(65) Prior Publication Data
US 2002/0091284 A1 Jul. 11, 2002

(30) Foreign Application Priority Data
Oct. 30, 2000 (FR) .............................. 00 13916

(51) Int. Cl.[7] .................. C07C 69/54; C07C 211/63
(52) U.S. Cl. ................. 560/222; 524/458; 524/460; 525/327.6; 526/318.44; 526/932; 564/282
(58) Field of Search ............ 560/222; 524/460, 524/458; 525/327.6; 526/932, 318.44; 564/282

(56) References Cited

U.S. PATENT DOCUMENTS

| | | | |
|---|---|---|---|
| 3,904,660 A | * | 9/1975 | Doss |
| 4,009,201 A | | 2/1977 | Steckler et al. |
| 6,171,505 B1 | * | 1/2001 | Maury et al. ............ 210/727 |
| 6,174,950 B1 | * | 1/2001 | Nzudie et al. ............ 524/460 |

FOREIGN PATENT DOCUMENTS

| EP | 0 839 767 A2 | 5/1998 |
|---|---|---|
| FR | 1.529.000 | 10/1968 |

* cited by examiner

Primary Examiner—Shailendra Kumar
(74) Attorney, Agent, or Firm—Millen, White, Zelano & Branigan, P.C.

(57) ABSTRACT

These compounds are represented by the formulae (Ia) and (Ib). To prepare them, in a first stage, p-xylene dichloride is reacted with a compound (II) to produce a compound (III) and, in a second stage, the compound (III) thus obtained is reacted with a compound of formula (IVa) or (IVb), resulting in an aqueous solution of the compound (Ia) or (Ib) respectively, the water of which is removed, if appropriate.

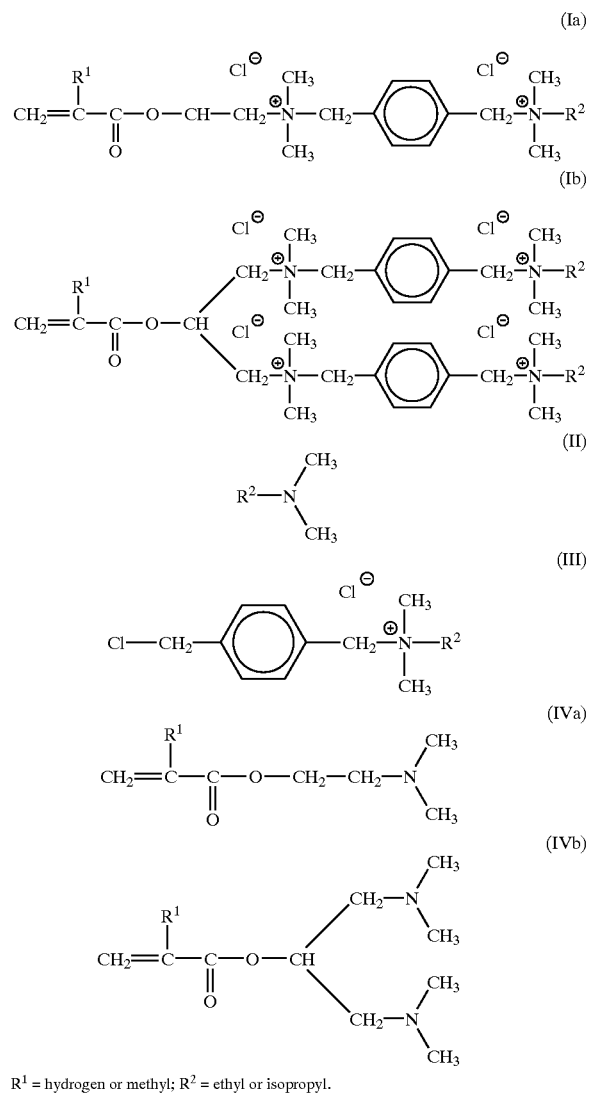

$R^1$ = hydrogen or methyl; $R^2$ = ethyl or isopropyl.

21 Claims, No Drawings

ACRYLATES COMPRISING SEVERAL QUATERNARY AMINO GROUPS IN THE ALCOHOL PART, THEIR PROCESS OF MANUFACTURE AND THE (CO) POLYMERS OBTAINED FROM THESE MONOMERS

The present invention relates to novel acrylate monomers comprising several quaternary amino groups in the alcohol part, to their process of manufacture and to the novel (co)polymers obtained from these novel monomers.

Compounds of the type of formula:

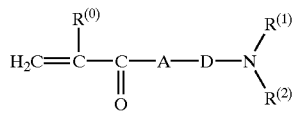

in which:
R$^{(0)}$ represents H or CH$_3$;
A represents —O— or —NH—;
D represents a linear or branched C$_1$–C$_6$ alkylene chain;
R$^{(1)}$ and R$^{(2)}$ which are identical or different, each independently represent H or C$_{1-5}$ alkyl;
are well known in the literature.

Important compounds of this family are N,N-dimethylaminoethyl acrylate (ADAME) and N,N-dimethylaminoethyl methacrylate (MADAME):

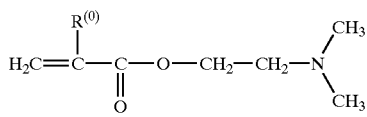

with R$^{(0)}$=H or CH$_3$.

A very extensive patent literature discloses the manufacture of aqueous solutions of quaternary ammonium salts from ADAME and MADAME, it being possible for these salts, for the most representative among them, to be represented by the formula:

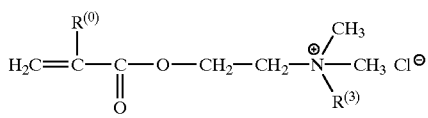

with R$^{(0)}$=H or CH$_3$ and R$^{(3)}$ =CH$_3$ or benzyl, it being possible for these salts to be denoted by the abbreviation (M)ADAMQUAT MC or (M)ADAMQUAT BZ, according to whether R$^{(3)}$ represents CH$_3$ or benzyl.

This reaction is a quaternization, in the presence of water, of the starting compound with a quaternizing agent R$^{(3)}$—Cl.

The aqueous solutions of quaternary salts thus obtained are used in particular to prepare polymers intended to act as cationic flocculents in water treatment.

Patent CZ-A-250 962 has disclosed compounds of formula:

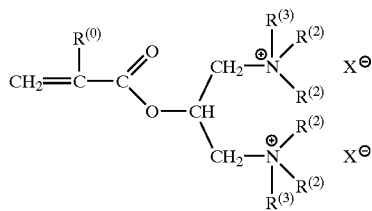

in which:
R$^{(0)}$ represents H or —CH$_3$;
R$^{(2)}$ represents —CH$_3$, —C$_2$H$_5$, —C$_3$H$_7$ or —C$_4$H$_9$;
R$^{(3)}$ represents —CH$_3$, —C$_2$H$_5$, —C$_3$H$_7$, —C$_4$H$_9$, —C$_6$H$_5$ or
—CH$_2$C$_6$H$_5$; and
X$^-$ represents Cl$^-$ or Br$^-$.

French Patent Application No. 00/00834 of Jan. 24, 2000 has also disclosed compounds of formula:

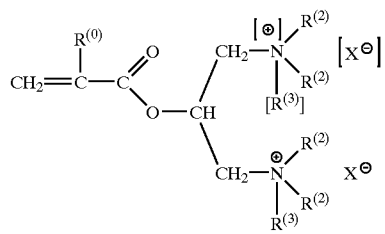

in which:
R$^{(0)}$ represents H or —CH$_3$;
R$^{(2)}$ represents —CH$_3$, —C$_2$H$_5$, —C$_3$H$_7$ or —C$_4$H$_9$; and the compound optionally being quaternized on one of the nitrogens; when the compound is quaternized on only one nitrogen, R$^{(3)}$ and X$^-$ have the following meanings: R$^{(3)}$ represents —CH$_3$ or —CH$_2$C$_6$H$_5$ and X$^-$ represents Cl$^-$ or CH$_3$OSO$_3^-$ or R$^{(3)}$ represents a C$_1$–C$_{12}$ alkyl group and X$^-$ represents Br$^-$ or I$^-$; when the compound is quaternized on both nitrogens, the two X$^-$ groups can be identical or different and the two R$^{(3)}$ groups can be identical, in which case R(3) represents a C$_5$–C$_{12}$ alkyl group and X$^-$ represents CH$_3$OSO$_3^-$, Br$^-$ or I$^-$, or different, in which case one of the R$^{(3)}$ groups represents —CH$_3$ or —CH$_2$C$_6$H$_5$ and X$^-$ represents Cl$^-$ or CH$_3$OSO$_3^-$ and the other represents a C$_5$–C$_{12}$ alkyl group and X$^-$ represents Br$^-$ or I$^-$.

These known monomers all make possible access to useful flocculents but with a cationicity which is regarded as still inadequate for some applications.

The Applicant Company has now discovered novel monomers which meet this expectation. These monomers thus form the subject-matter of the present invention, as do their process of manufacture and the homo- or copolymers comprising units derived from these novel monomers.

A subject-matter of the present invention is thus first a compound of formula (Ia) or (Ib):

(Ia)

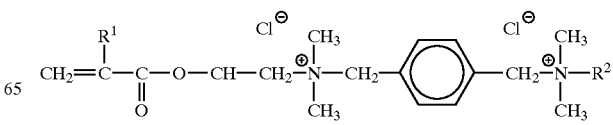

-continued

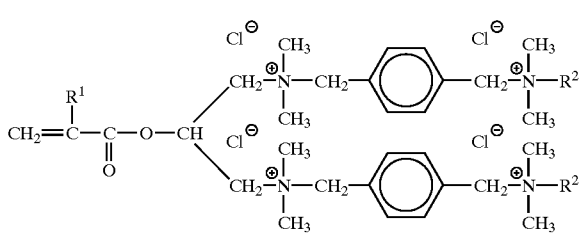
(Ib)

in which:

R[1] represents hydrogen or methyl; and
R2 represents ethyl or isopropyl.

The compounds of the invention can advantageously be provided in aqueous solution, having a concentration of compound (Ia) or (Ib) which is in particular from 60 to 80% by weight.

Another subject-matter of the present invention is a process for the manufacture of the compound of formula (Ia) or (Ib) as defined above, characterized in that:

in a first stage, p-xylylene dichloride:

is reacted with a compound of formula (II):

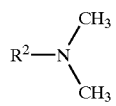
(II)

in which $R^2$ is as defined above,
to produce a compound of formula (III):

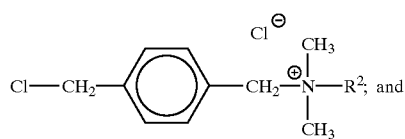
(III)

in a second stage, the compound of formula (III) thus obtained is reacted with a compound of formula (IVa) or (IVb):

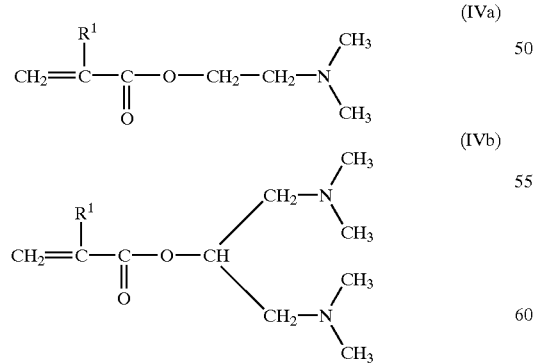

in which $R^1$ is as defined above,
resulting in an aqueous solution of the compound (Ia) or (Ib) respectively, the water of which is removed, if appropriate.

In the first stage, the reaction is generally carried out in a solvent medium, such as tetrahydrofuran, with a molar ratio of the p-xylylene dichloride to the compound (II) of 0.8 to 1.2, preferably 0.9 to 1.1, at a temperature of 5 to 60° C., preferably of 15 to 40° C., for a period of time ranging from 8 to 144 hours, preferably from 10 to 96 hours.

The product is obtained in the form of colourless crystals.

The reaction of the second stage is carried out with a molar ratio of the compound (III) to the compound (IVa) or (IVb) of between 0.95 and 2.1, according to the situation, at a temperature of 30 to 70° C., preferably of 40 to 55° C., for a period of time of 0.5 to 8 hours, preferably of 1 to 6 hours.

Furthermore, the second stage is generally carried out in the presence of at least one stabilizer chosen in particular from hydroquinone methyl ether, 3,5-di(tert-butyl)-4-hydroxytoluene and hydroquinone, and mixtures of these stabilizers, in a proportion of 100 to 2 000 ppm with respect to the charge.

Another subject-matter of the present invention is homopolymers or copolymers comprising units of at least one monomer of formula (Ia) or (Ib) as defined above.

The copolymers based on the monomers (Ia) and (Ib) can be water-soluble or hydrophobic polymers presented in the form of an aqueous dispersion, latex, aqueous solution, inverse emulsion or powder. They are prepared by radical copolymerization by various synthetic processes, such as dispersion, solution, direct emulsion, inverse emulsion, inverse suspension and water-in-water polymerization processes.

The present invention also relates to the compounds of formula (III) as defined above as intermediate compounds in the preparation of the compounds (I).

The following examples illustrate the present invention without, however, limiting the scope thereof. The percentages are by weight, unless otherwise indicated. In these Examples, the following abbreviations have been used:

*THF: tetrahydrofuran
*ADAME: N,N-dimethylaminoethyl acrylate
*S-ADAME: 2-(dimethylamino)-1-(dimethylaminomethyl)-ethyl acrylate
*HQME: hydroquinone methyl ether

EXAMPLE 1

Synthesis of 4-(Chloromethyl)-N-ethyl-N,N-dimethylbenzenemethanaminium Chloride

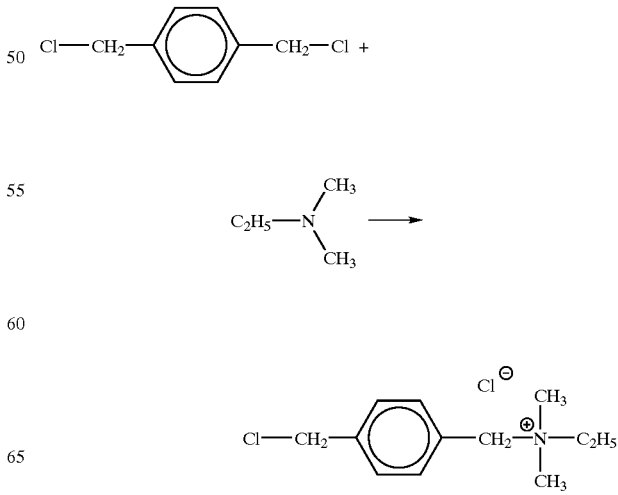

8.75 g (50.0 mmol) of p-xylylene dichloride and 100 ml of THF were placed in a 250ml three-necked round-bottomed flask equipped with a thermometer and a mechanical stirrer. The mixture was stirred until all the solids had been dissolved (its temperature fell to 15° C. at this time) and 5.64 ml (52.5 mmol) of N-ethyl-dimethylamine were immediately added.

The round-bottomed flask was subsequently closed using a glass stopper and its contents were stirred for 4 days at 35° C., samples of the filtered reaction solution being analysed after 1 day and 4 days. The final sample exhibited a conversion of the starting material of 92%.

The precipitate was collected by filtration and dried under vacuum for 30 minutes at ambient temperature to give 10.56 g of the expected product in the form of colourless crystals (85% yield).

$^1$H NMR (CDCl$_3$): δ7.8–7.3 (m, 4H), 5.09 (s, 2H), 4.56 (s, 2H), 3.66 (q, 2H), 3.25 (s, 6H), 1.43 (t, 3H).

$^{13}$C NMR (CDCl$_3$): δ140.2(s), 134.0(d), 129.4(d), 128(s), 66.6(t), 59.5(t), 49.1(q), 45.6(t), 8.9(q).

EXAMPLE 2

Synthesis of 4-(Chloromethyl)-N-isopropyl-N,N-dimethylbenzenemethan-aminium Chloride

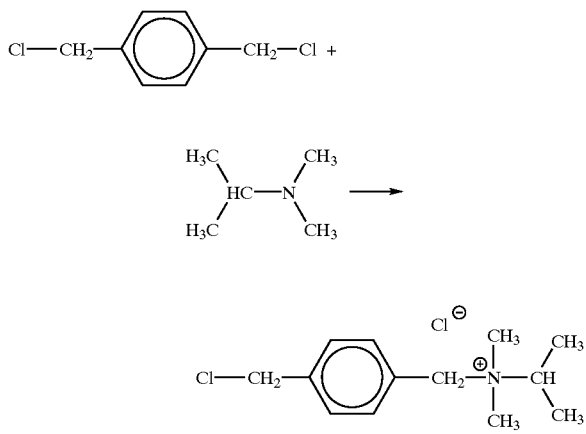

8.75 g (50.0 mmol) of p-xylylene dichloride and 100 ml of THF were placed in a 250 ml three-necked round-bottomed flask equipped with a thermometer and a mechanical stirrer. The mixture was stirred until all the solids had dissolved (its temperature fell to 15° C. at this point) and 6.39 ml (52.5 mmol) of N-isopropyl-dimethylamine were immediately added.

The round-bottomed flask was subsequently closed using a glass stopper and its contents were stirred for 4 days at 45° C., samples of the filtered reaction solution being analysed after 1 day and 2 days and at the end. The final sample exhibited a conversion of the starting material of 87%. The precipitate was collected by filtration and dried for 3 hours at ambient temperature and 1.99×10$^3$ Pa (15 mmHg) to give 10.35 g of the expected product in the form of colourless crystals (79% yield).

$^{13}$C NMR (D$_2$O): δ140.0(s), 133.6(d), 129.7(d), 127.8(s), 66.6(d), 64.5(t), 47.0(q), 45.6(t), 45.8(t), 16.4(q).

EXAMPLE 3

Synthesis of N-Acryloyloxyethyl-N'-ethyl-N,N,N', N'-tetramethylbenzene-1,4-dimethanaminium Dichloride

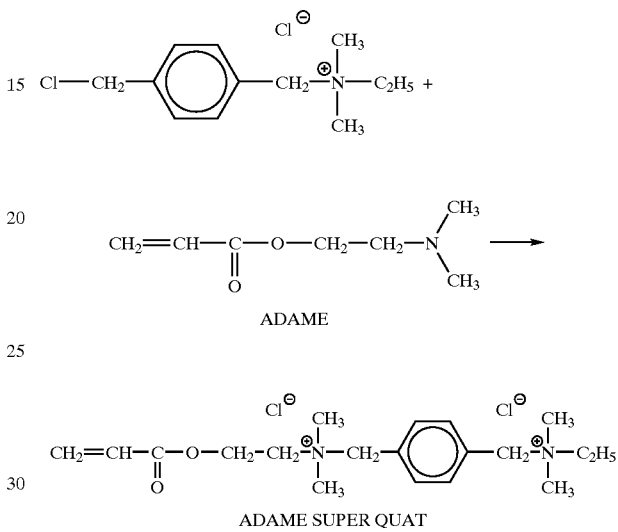

8.00 g (32.3 mmol) of the compound obtained in Example 1, 4.61 g (32.3 mmol) of ADAME, 4.20 g of water and 16.8 mg (1000 ppm) of HQME were placed in a large-mouthed 25 ml glass flask equipped with a cap and a magnetic stirrer bar.

The mixture was subsequently stirred without either heating or cooling. The internal temperature first of all rose to 50° C. because of the exothermic effect and then it began to fall. After stirring for 3 hours at ambient temperature, a very viscous homogeneous mixture had formed and the analysis of ionic chloride showed that the reaction was complete (100% conversion). A quantitative yield of the expected product was obtained in the form of a 75% solution in water. Its structure was confirmed by NMR analysis.

$^{13}$C NMR (D$_2$O): δ165.0(s), 134.2(d), 134.1(d), 133.8(t), 130.4(s), 129.7(s), 127.4(d), 68.7(t), 66.9(t), 63.3(t), 60.6(t), 58.7(t), 50.9(q), 49.6(q), 8.2(q).

EXAMPLE 4

Synthesis of N-Acryloyloxyethyl-N'-isopropyl-N,N, N',N'-tetramethylbenzene-1,4-dimethanaminium Dichloride

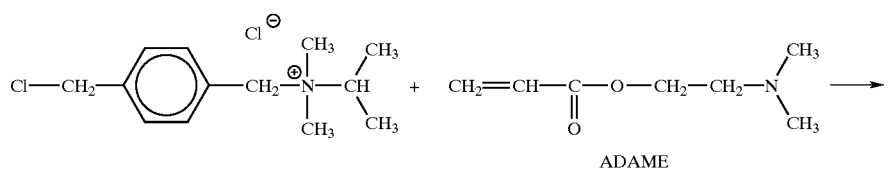

-continued

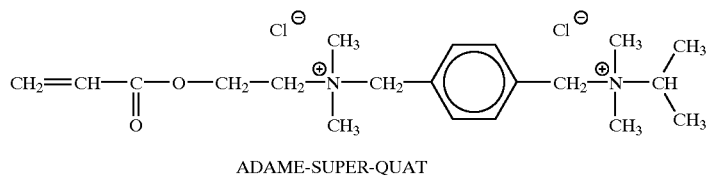

ADAME-SUPER-QUAT 4.90 g (18.7 mmol) of the compound obtained in Example 2, 2.67 g (18.7 mmol) of ADAME, 2.52 g of water and 10.1 mg (1 000 ppm) of HQME were placed in a large-mouthed 25 ml glass flask equipped with a cap and a magnetic stirrer bar.

The mixture was subsequently stirred without either heating or cooling. The internal temperature first of all rose to 50° C. because of the exothermic effect and then it began to fall. After stirring for 1 hour at ambient temperature, a very viscous homogeneous mixture had formed and the analysis of ionic chloride showed that the reaction was complete (100% conversion). A quantitative yield of the expected product was obtained in the form of a 75% solution in water. Its structure was confirmed by NMR analysis.

$^{13}$C NMR (D$_2$O): δ167.6(s), 134.2(d), 134.1(d), 133.8(t), 130.6(s), 129.6(s), 127.3(d), 68.8(t), 67.0(d), 63.2(t), 59.1(t), 58.6(t), 50.8(q), 47.2(q), 16.4(q).

EXAMPLE 5

Synthesis of N,N-(2-Acryloyloxypropane-1,3-diyl) bis(N'-isopropyl-N, N,N',N'-tetramethylbenzene-1,4-dimethanaminium) Tetrachloride

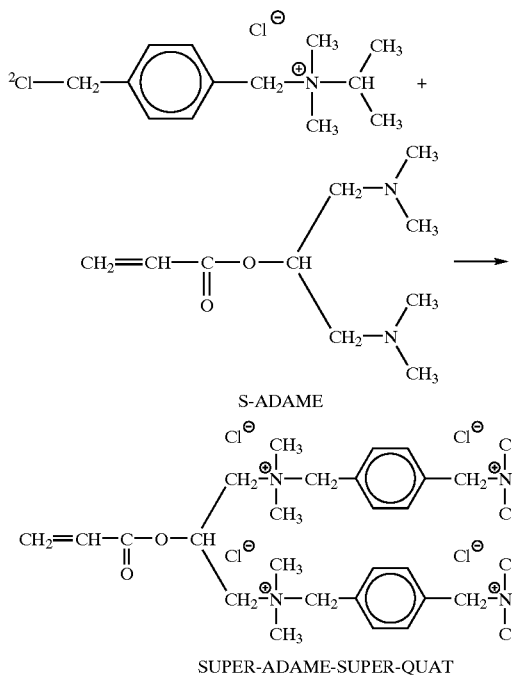

5.00 g (19.1 mmol) of the compound obtained in Example 2, 1.87 g (9.35 mmol) of S-ADAME, 2.26 g of water and 9.03 mg (1000 ppm) of HQME were placed in a large-mouthed 25 ml glass flask equipped with a cap and a magnetic stirrer bar.

The mixture was subsequently stirred without either heating or cooling. The internal temperature first of all rose to 40–45° C. because of the exothermic effect and then it began to fall. After stirring for 30 minutes at ambient temperature, a homogeneous mixture too viscous to be stirred had been formed. A further 0.64 g of water was added to liquefy the reaction mixture and, after stirring for a further 30 minutes, analysis of ionic chloride showed that the reaction was complete. A quantitative yield of the expected product was obtained in the form of a 70% solution in water.

$^{13}$C NMR (D$_2$O): δ166.4(s), 136.8(t), 134.3(d), 134.2(d), 130.8(s), 129.0(s), 126.5(d), 70.0(t), 67.0(d), 66.1(t), 64.4(t), 63.8(d), 51.2(q), 50.7(q), 47.3(q), 16.4(q).

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 00/13.916, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compound of formula (Ia) or (Ib):

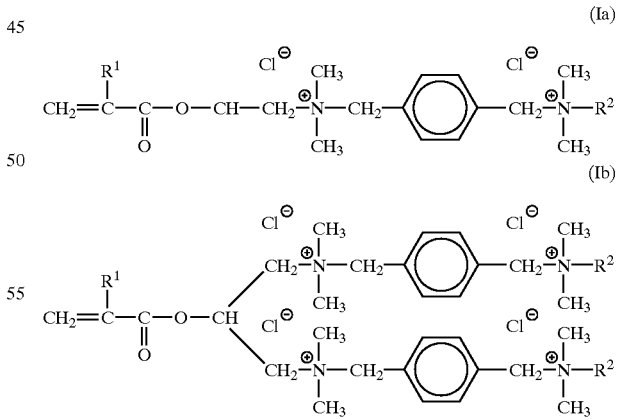

in which:

R$^1$ represents hydrogen or methyl; and

R$^2$ represents ethyl or isopropyl.

2. An aqueous solution of at least one compound according to claim 1, having a concentration of compound (Ia) or (Ib) of from 60 to 80% by weight.

3. A process for the manufacture of a compound of formula (Ia) or (Ib) as defined in claim 1 comprising:

in a first stage, p-xylylene dichloride:

is reacted with a compound of formula (II):

in which $R^2$ is as defined in claim 1, to produce a compound of formula (III):

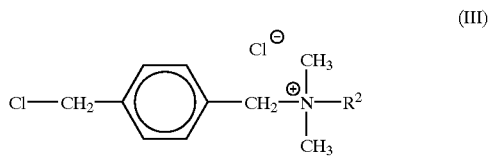

in a second stage, the compound of formula (III) thus obtained is reacted with a compound of formula (IVa) or (IVB):

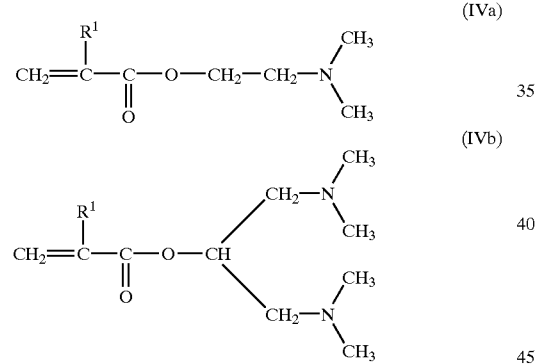

in which $R^1$ is as defined in claim 1, resulting in an aqueous solution of the compound (Ia) or (Ib) respectively.

4. Process according to claim 3, characterized in that in the first stage, the reaction is carried out in a solvent medium.

5. Process according to claim 4, characterized in that the solvent is tetrahydrofuran.

6. A process according to claim 3, wherein the first stage is carried out with a molar ratio of the p-xylylene dichloride to the compound of formula (II) of 0.8 to 1.2.

7. A process according to claim 3, wherein the first stage is carried out at a temperature of 5 to 60° C. for a period of time of 8 to 144 hours.

8. A process according to claim 3, wherein the compound of formula (III) is obtained in the form of colorless crystals.

9. A process according to claim 3, wherein the second stage is carried out with a molar ratio of the compound of formula (III) to the compound of formulae (IVa) or (IVb) of between 0.95 and 2.1.

10. A process according to claim 3, wherein the second stage is carried out at a temperature of 30 to 40° C. for a period of time of 1 to 6 hours.

11. A process according to claim 3, wherein the second stage is carried out in the presence of at least one stabilizer selected from the group consisting of hydroquinone methyl ether, 3,5-di (tert-butyl)-4-hydroxytoluene and hydroquinone, and mixtures of these stabilizers, in a proportion of 100 to 2 000 ppm with respect to the charge.

12. A homopolymer or copolymer comprising units of at least one monomer of formula (Ia) or (Ib) as defined in claim 1.

13. A compound of formula III

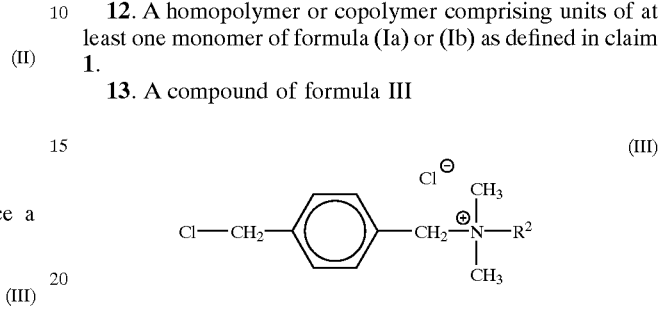

wherein $R^2$ represents ethyl or isopropyl.

14. A compound according to claim 13, wherein said compound is in the form of colorless crystals.

15. A process for producing a compound of claim 1, comprising reacting a compound of formula III

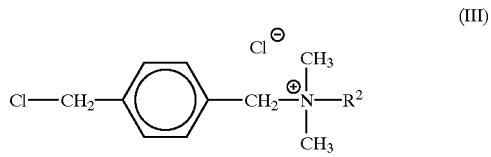

wherein $R^2$ is ethyl or isopropyl, with a compound of formula (IVa) or (IVb):

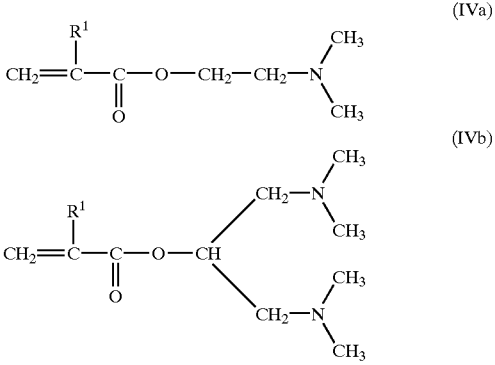

16. A compound according to claim 1, being compound (Ia).

17. A compound according to claim 1, wherein said compound is of formula (Ib).

18. A compound according to claim 14, wherein $R^2$ is ethyl.

19. A compound according to claim 14, wherein $R^2$ is isopropyl.

20. A process according to claim 15, wherein $R^2$ is ethyl.

21. A process according to claim 15, wherein $R^2$ is isopropyl.

* * * * *